United States Patent [19]

Kuroiwa et al.

[11] Patent Number: 5,081,274
[45] Date of Patent: Jan. 14, 1992

[54] 4-ACYL-2,6-DIHALOPHENYL-PHOSPHORIC ACID DERIVATIVES USEFUL IN THE DETERMINATION OF ACID PHOSPHATASE ACTIVITY

[75] Inventors: Katsumasa Kuroiwa; Katsuhiro Katayama; Toshihide Miura, all of Koriyama; Takeshi Nagasawa, Urawa, all of Japan

[73] Assignee: Nitto Boseki Co., Ltd., Fukushima, Japan

[21] Appl. No.: 409,049

[22] Filed: Sep. 19, 1989

[30] Foreign Application Priority Data

Sep. 19, 1988 [JP] Japan .................. 63-234555
May 22, 1989 [JP] Japan .................. 1-128431

[51] Int. Cl.$^5$ .............................................. C07F 9/12
[52] U.S. Cl. ................................................ 558/198
[58] Field of Search ................................... 558/198

[56] References Cited

U.S. PATENT DOCUMENTS 3,379,732  4/1968  Faith et al. ...................... 260/297
4,719,097  1/1988  Muhlegger et al. ................... 424/2

FOREIGN PATENT DOCUMENTS 0271731  6/1988  European Pat. Off. .

OTHER PUBLICATIONS

*J. Biol. Chem.*, 101:93–104 (1933).

*J. Vrol.* 58:89, (1947).
*Canad. Med. Assoc. J.* 31: 376, (1934).
*J. Clin. Path.*, 7:322 (1954).
*Clin. Chem. Acta.*, 168: 231 (1987).
Owen et al., Preparation of Aryl and 2,2,2-Trihaloethyl Dihydrogen Phosphates, *Synthesis*, 1974 (10), 704–705.

*Primary Examiner*—Mary C. Lee
*Assistant Examiner*—Michael G. Ambrose
*Attorney, Agent, or Firm*—Darby & Darby

[57] ABSTRACT

Phosporic acid derivatives represented by formula (I):

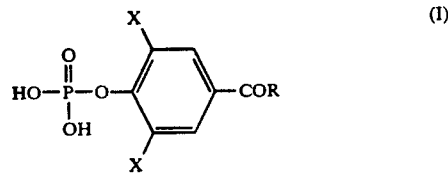

wherein X is a halogen and R is —(CH$_2$)$_n$CH$_3$ (n=0 to 3), or salts thereof are stable to non-enzymatic hydrolysis and are capable of specifically reacting with acid phosphatase. Therefore, the activity of acid phosphatase in the sample can be determined extremely accurately by reacting said compound with a sample containing acid phosphatase and quantitatively determining the reaction product by colorimetry.

4 Claims, 9 Drawing Sheets

U.V SPECTRUM

IR SPECTRUM

REACTION TIME COURSE

SUBSTRATE STABILITY IN BUFFER (37 °C)

REACTION TIME COURSE

REACTION TIME COURSE

4-ACYL-2,6-DIHALOPHENYL-PHOSPHORIC ACID DERIVATIVES USEFUL IN THE DETERMINATION OF ACID PHOSPHATASE ACTIVITY

BACKGROUND OF THE INVENTION

1. Field of the Invention

The present invention relates to novel phosphoric acid derivatives and a method for determination of acid phosphatase activity using the same. According to the present invention, acid phosphatase activity can be accurately determined in a simple way, and the present invention is extremely useful as an assay for determining acid phosphatase in the fields of medical treatment and laboratory procedures.

2. Related Art Statement

Acid phosphatase (hereafter referred to as Acp) is an enzyme that hydrolyzes a phosphoric acid monoester under acidic conditions (pH of 4 to 6). In patients with prostatic cancer, breast cancer accompanied by bone metastasis or bone diseases, and liver and renal diseases, an increase of Acp in serum or urine is noted; and, attention has been brought to determination of Acp as a tumor marker.

So far, methods using various synthetic substrates as shown below have been reported for assaying acid phosphatase activity. Some of them have been practically applied to ordinary laboratory procedures.

(a) Method using β-glycerophosphoric acid as substrate [Bodansky, A.: J. Biol. Chem., 101, 93 (1933)]:

Hydrolysis of β-glycerophosphoric acid by Acp gives glycerine and inorganic phosphorus. The inorganic phosphorus is allowed to produce a color and the color is measured.

(b) Method using p-nitrophenylphosphoric acid as substrate [Hudson, P.B.: J. Urol., 58, 89 (1947)]:

Hydrolysis of p-nitrophenylphosphoric acid by Acp gives p-nitrophenol, which is reacted with an alkali to form a color and the color is measured.

(c) Method using phenylphosphoric acid as substrate:

There are a method which comprising hydrolyzing phenylphosphoric acid with Acp and reacting the resulting phenol with Folin-Ciocalten reagent [King, E.J., Armstrong, A.R.: Canad. Med. Assoc. J., 31, 376 (1934)] and a method which comprises hydrolyzing phenylphosphoric acid with Acp, oxidatively condensing the resulting phenol with 4- aminoantipyrine and measuring the formed quinone of a red color [Kind, P.R.N., King, E.J.: J. Clin. Path., 7, 322 (1954)].

(d) Method using naphthylphosphoric acid as substrate [Hillman, G.: Z. Klin. Chem., Klin. U. Biochem., 9, 237 (1971)]:

Naphthol formed by hydrolysis with Acp is reacted with Fast Red TR to form an azo dye and the azo dye is colorimetrically determined.

(e) Method using 2,6-dichloro-4-nitrophenylphosphoric acid as substrate [Teshima, S., Hayashi, Y., Ando, M.: Clin. Chim. Acta., 168, 231 (1987)]:

A yellow hue of 2,6-dichloro-4-nitrophenol formed by hydrolysis with Acp is colorimetrically determined at 400nm.

These assay methods involve various problems and the problems are causes for inaccuracy of measurement data. For example, in method (a), inorganic phosphorus is contained in normal serum and hence, the inorganic phosphorus in serum to be tested must be previously assayed. Furthermore, complicated operations are required and such are problems in practical application. In method (b), after the enzymatic reaction in an acidic region which is the optimum pH of Acp, the system should be rendered alkaline with sodium hydroxide aqueous solution, etc., otherwise p-nitrophenol as a chromophore does not form a color and it is thus impossible to perform rate assay. Furthermore, the wavelength at 405 nm to be measured corresponds to a slope of U.V. spectrum of the chromophore and is seriously affected by bilirubin in serum, resulting in a cause for erroneous measurement data. Method (c) requires a color-forming reaction of phenol formed by hydrolysis with Acp as in method (b). It is thus impossible to conduct rate assay. In addition, the color formation between phenol and 4-aminoantipyrine is also unstable and this is another cause for error. In method (d), Fast Red TR which is reacted with free naphthol is unstable. Furthermore, the method involves a large lag time in the reaction which causes an error in measurement data, although the method may also be applicable to rate assay and to an automated analysis device.

Method (e) enables one to perform rate assay without requiring any color-forming reaction and is also applicable to automated analysis instruments. However, the method is liable to be affected by bilirubin or hemoglobin in serum since the wavelength for the measurement is close to 400 nm. In addition, the substrate itself is unstable in an aqueous solution and causes spontaneous hydrolysis.

As described above, the conventional methods for determining Acp activity involves various defects and the defects cause incorrect measurement data. Therefore, these methods are practically disadvantageous.

SUMMARY OF THE INVENTION

Accordingly, an object of the present invention is to provide novel phosphoric acid derivatives or salts thereof which are extremely stable to non-enzymatic hydrolysis, have a characteristic of specifically reacting with Acp in serum and are extremely useful for determination of Acp activity.

Another object of the present invention is to provide a method for determination of acid phosphatase activity using the novel phosphoric acid derivatives or salts thereof.

These and other objects and advantages will be apparent from the following description.

A first aspect of the present invention is concerned with novel phosphoric acid derivatives represented by formula (I):

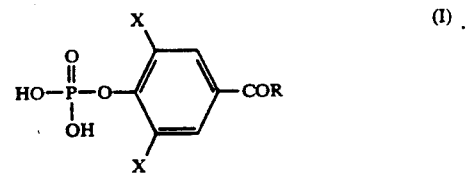

wherein X is a halogen and R is —(CH$_2$)$_n$CH$_3$ (n=0 to 3), or salts thereof.

A second aspect of the present invention is concerned with a method for determination of acid phoshatase activity using the novel phosphoric acid derivatives or salts thereof as substrates.

DETAILED DESCRIPTION OF THE INVENTION

In the formula (I) described above, examples of R include methyl, ethyl, propyl, and butyl. X represents a halogen exemplified by chlorine, bromine, fluorine, etc. Examples of the salts of novel phosphoric acid derivative represented by formula (I) described above include alkali metal salts such as sodium salts, potassium salts, etc.; amine salts such as tris(hydroxy-methyl)aminomethane salts, cyclohexylamine salts, dicyclohexylamine salts, etc.

The novel phosphoric acid derivatives can be synthesized, for example, by the following reaction scheme:

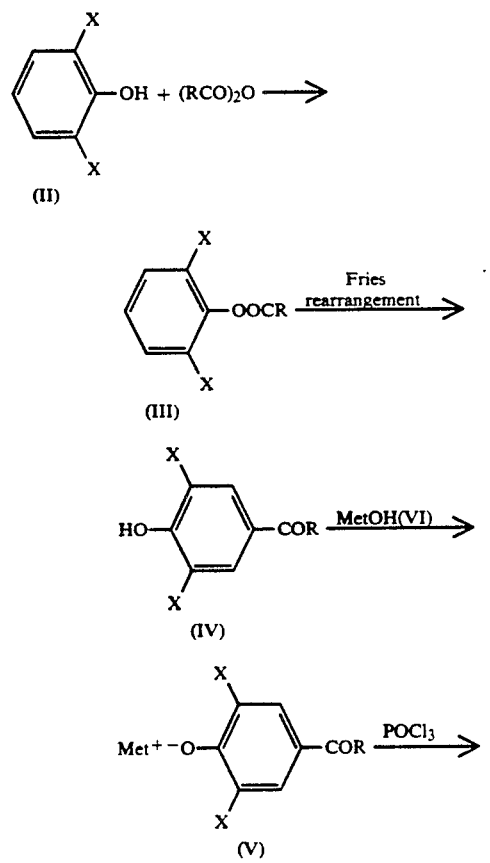

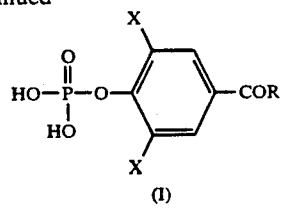

That is, the novel phosphoric acid derivative of formula (I) can be obtained by reacting a 2,6-dihalophenol (II) with an acid anhydride to esterify, then subjecting the resulting 2,6-dihalophenol ester (III) to Fries rearrangement in the presence of a catalyst such as aluminum chloride, zinc chloride, etc., reacting the formed 2,6-dihalo-4-acylphenol (IV) with an alkali metal hydroxide [MetOH (VI)] such as sodium hydroxide, potassium hydroxide, etc. to give the corresponding salt (V), and then reacting the salt (V) with phosphorus oxychloride (POCl3) to effect hydrolysis. These reactions are all known and conventional and the reaction conditions are identical with those of the known reactions.

The salts of the novel phosphoric acid derivatives can be obtained by treating the compounds of formula (I) with alkali metal hydroxides such as sodium hydroxide, potassium hydroxide, etc.; amines such as tris(hydroxymethyl)aminomethane, cyclohexylamine, etc. in a conventional manner.

Next, the method for determination of Acp activity of the present invention using the novel phosphoric acid derivative is described below by referring to 2,6-dichloro-4-acetylphenylphosphoric acid (hereafter referred to as DCAP-P).

Figure 1:
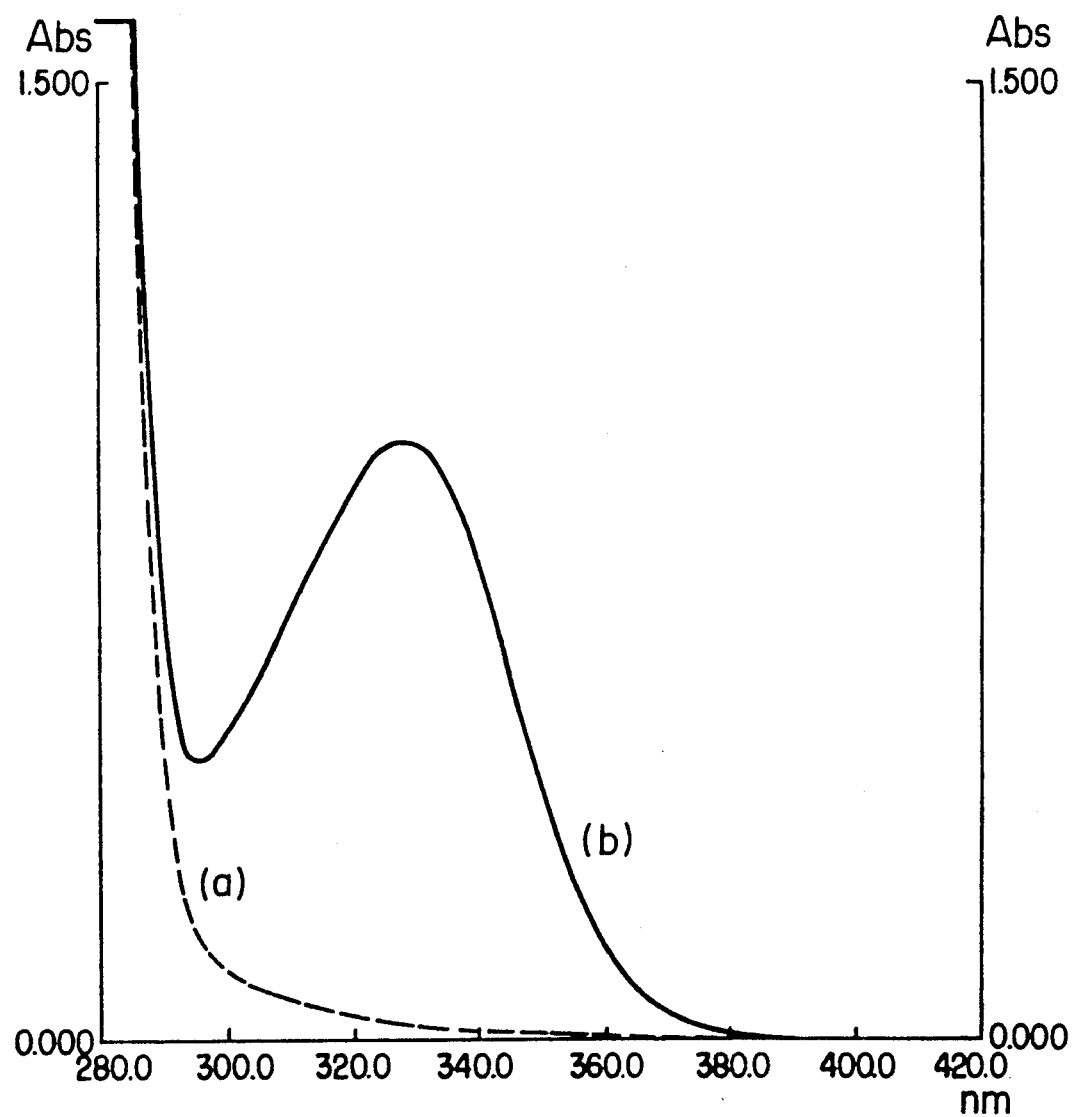
FIG. 1 shows U.V. spectra of (a) DCAP-P (concentration of 50 μM) and (b) 2,6-dichloro-4-acetylphenol (concentration of 50 μM) in 100 mM sodium citrate buffer solution at pH 5.4 (25° C.).

U.V. spectra of (a) DCAP-P and (b) 2,6-dichloro-4-acetylphenol are shown in FIG. 1. When DCAP-P is hydrolyzed by the action of Acp, 2,6-dichloro-4-acetylphenol is formed. Phosphoric acid and DCAP-P have little U.V. absorption at 300 nm or more. 2,6-Dichloro-4-acetylphenol absorbs U.V. below 370 nm. Therefore, in the method for determining Acp activity by the U.V. method, the reaction can be traced at a measurement wavelength ranging from 300 to 370 nm, using DCAP-P as a substrate. In this case, interference of other serum components is minimized. Accordingly, the increase of 2,6-dichloro-4-acetylphenol can be accurately traced so that the Acp activity can be accurately determined. Furthermore, as will be later described, DCAP-P has many excellent advantages.

Thus, a specific example of the method for determination of Acp activity using the novel phosphoric acid derivative of formula (I) includes the following procedure. That is, the method comprises mixing a sample containing Acp with the novel phosphoric acid derivative represented by formula (I) or salts thereof to cause an enzyme reaction and then measuring absorbance of the reaction product, especially at 300 to 370 nm, whereby the Acp activity can be determined.

According to the method described above using 2,6-dichloro-4-nitrophenylphosphoric acid as a substrate, rate assay can be made in the acidic region which is the optimum pH of Acp. However, the measurement is made at the wavelength of 400 nm so that the data are strongly interfered by bilirubin and hemoglobin which are serum components. To the contrary, the wavelength of approximately 300 to 370 nm adopted in the present invention is little interfered by these components and hence, it is easy to select the optimum conditions for the measurement. In addition, for example, 2,6-dichloro-4-acetylphenol which is formed by hydrolysis of the novel phosphoric acid derivative of the present invention, for example, DCAP-P, has the maximum absorption near 300 nm and thus, the wavelength for measurement can be set at the peak. This implies that differences in molecular extinction coefficient, etc. generated from the question of accuracy in wavelength of an analysis device are reduced as less as possible and differences in measurement data dependent on types of analysis devices are extremely minimized.

Figure 5:
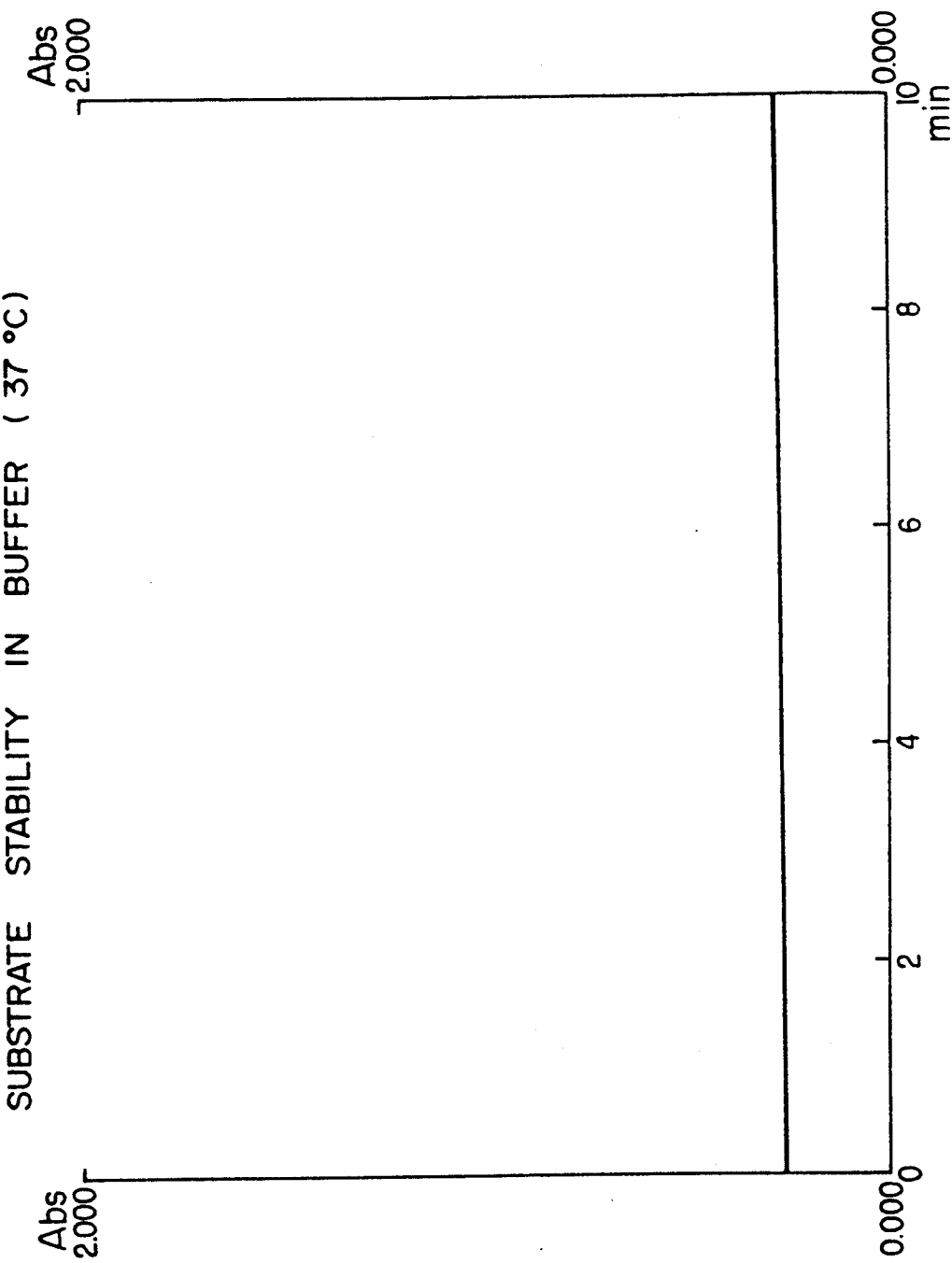
FIG. 5 shows stability of DCAP-P to non-enzymatic hydrolysis.

In addition, the novel substrate of the present invention, for example, DCAP-P, is very stable to non-enzymatic hydrolysis For example, under conditions at 37° C. for 10 minutes in 10 mM citrate buffer solution showing pH of 5.4, hydrolysis hardly occurred (FIG. 5). The results indicate that non-enzymatic hydrolysis can be ignored during the measurement but the Acp activity can be accurately determined.

Furthermore, the novel phosphoric acid derivative of the present invention has a high affinity to Acp and is suited for the determination of Acp activity.

As a buffering agent for maintaining the pH at a constant level in the determination of Acp activity, citric acid, acetic acid, succinic acid, phthalic acid, etc. may be used. Buffering agents other than those described above may also be usable so long as they can maintain the buffering ability in a pH range of from 4.0 to 6.0.

Figure 4:
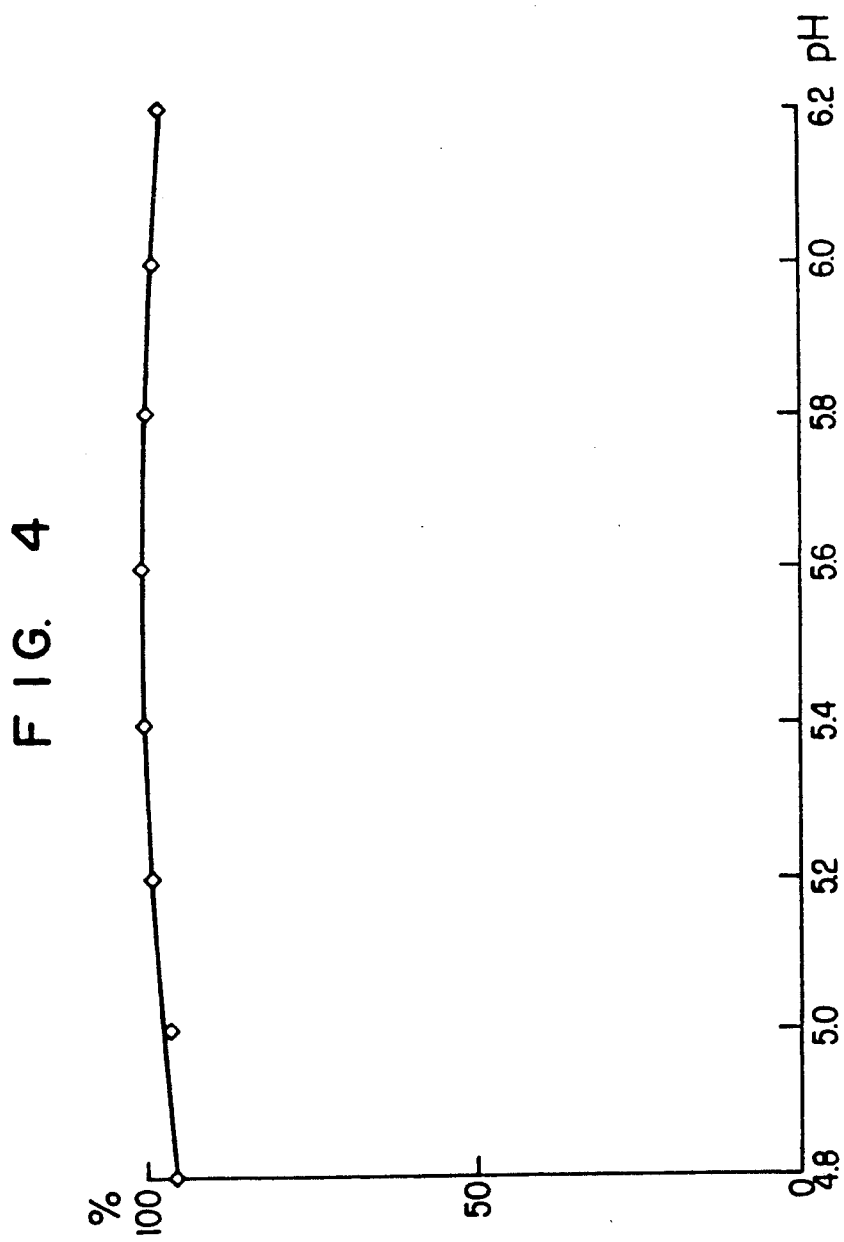
FIG. 4 shows the optimum pH of Acp.

In the case of using, for example, DCAP-P, as a substrate, the optimum pH of Acp was about 5.4 in 100 mM citrate buffer solution (cf. FIG. 4). As stated above, since DCAP-P is stable to non-enzymatic hydrolysis at pH of 5.4, the reactions can be carried out at the optimum pH of Acp according to the method for determination of the present invention.

The method for determination of Acp activity according to the present invention can solve the problems of the conventional methods in various points. The advantages of the present invention are given below.

(1) The reaction mechanism in the measurement system is simple and clear so that causes for error in measurement data are extremely less.

(2) The measurement can be made at the peak wavelength (330 nm).

(3) The novel phosphoric acid derivative, for example, DCAP-P, of the present invention which is used as the substrate is very stable to non-enzymatic hydrolysis and hence, reproducibility of the measurement data is good.

(4) It is unnecessary to correct the data of a sample using a blank sample so that the measurement can be made rapidly in a simple manner and a large number of samples can be treated.

(5) Since the novel phosphoric acid derivative, for example, DCAP-P, of the present invention is stable, the reactions can be carried out at the optimum pH (5.4).

(6) Since the molecular extinction coefficient of, for example, 2,6-dichloro-4-nitrophenol, formed by hydrolysis of for example, DCAP-P, which is the novel phosphoric acid derivative of the present invention, is sufficiently large in the measurement wavelength at the optimum pH (5.4) of Acp, the reactions can be continuously traced, without temporarily terminating the reaction, rendering the system alkaline, and then performing colorimetry as required for the case of using p-nitrophenol.

(7) The method is readily applicable to an automated analysis device.

(8) The novel phosphoric acid derivative of the present invention has a high affinity to Acp and is suited for the determination of Acp activity.

As described above, the method for determination of Acp activity according to the present invention has solved the problems encountered in the prior art methods and has many advantages and characteristic properties so that the Acp activity can be accurately determined in a simple way. Therefore, the present invention can sufficiently contribute to the determination of Acp activity in daily laboratory procedures.

Hereafter the present invention is described in more detail with reference to the examples below but is not deemed to be limited thereto.

EXAMPLE 1

Synthesis of 2,6-dichloro-4-acetylphenylphosphoric acid (1) In 28 ml of acetic anhydride was dissolved 50.0 g of 2,6-dichlorophenol and, one or two drops of conc. sulfuric acid were added to the solution The mixture was reacted at 130° C. for 10 minutes to effect acetylation After the reaction, the reaction solution was poured onto 300 ml of ice water and the mixture was extracted with ethyl acetate After drying the ethyl acetate phase over anhydrous magnesium sulfate overnight, the ethyl acetate phase was concentrated to give 58.2 g of colorless oily substance. Next, the oily substance was dissolved in 150 ml of nitrobenzene and 56 8 g of powdery aluminum chloride was gradually added to the solution. The reaction was carried out at 60° to 70° C. for 27 hours to effect Fries rearrangement. After completion of the reaction, the reaction solution was poured onto 1 liter of cold dil. hydrochloric acid and the organic phase was separated from the aqueous phase. The organic phase was extracted with 2N sodium hydroxide aqueous solution After the extraction, the solution was rendered acidic by adding 5N hydrochloric acid thereto followed by extracting with ethyl acetate. After drying over anhydrous magnesium sulfate, the ethyl acetate phase was concentrated to give 38.5 g of 2,6-dichloro-4-acetylphenol as crude crystals. The crystals were recrystallized from hot ethyl acetate to give 19.9 g of pure white 2,6-dichloro-4-acetylphenol. 2,6-dichloro-4-acetylphenol (3,5-dichloro-4-hydroxyacetophenone): $C_8H_6Cl_2O_2$ m.p. 160°–162° C.

| | Elemental analysis [%] | |
|---|---|---|
| | Found | Calcd. |
| C: | 47.05 | 46.86 |
| H: | 2.78 | 2.95 |

(2) In acetone was dissolved 8.9 g of 2,6-dichloro-4-acetylphenol and, 10.8 ml of 2N sodium hydroxide aqueous solution was added to the solution under ice cooling.

Acetone and ether were again added to the solution to precipitate crystals. The crystals were taken out by filtration and dried under reduced pressure to give 8.04 g of light yellow 2,6-dichloro-4-acetylphenol sodium salt. Then, 2.61 g of the sodium salt was gradually added to 10.4 ml of phosphorus oxychloride cooled to about 10° C. After the addition, the reaction was carried out at 12 to 15° C. After the precipitated sodium chloride was removed by filtration, the filtrate was concentrated to give a brown oily substance. To the oily substance was added about 100 ml of chilled water to perform hydrolysis at 0° C. to room temperature for 45 minutes. After insoluble matters were removed by filtration, the filtrate was extracted with ethyl minutes After drying over anhydrous magnesium sulfate, the ethyl acetate phase was concentrated to give 1.22 g of 2,6-dichloro-4-acetylphenylphosphoric acid as crude crystals. The crude crystals were recrystallized from hot ethyl acetate/n-hexane to give 682 mg of crystals The crystals were further purified by column chromatography (fixed phase: Sephadex ® LH-20, solvent: methanol) to give 521 mg of 2,6-dichloro-4-acetylphenylphosphoric acid as white crystals. 2,6-Dichloro-4-acetylphenylphosphoric acid:

$C_8H_7Cl_2O_5P$ m.p. 165°–170° C. (dec.)

| | Elemental analysis [%] | |
|---|---|---|
| | Found | Calcd. |
| C: | 33.38 | 33.71 |
| H: | 2.53 | 2.48 |

Figure 2:
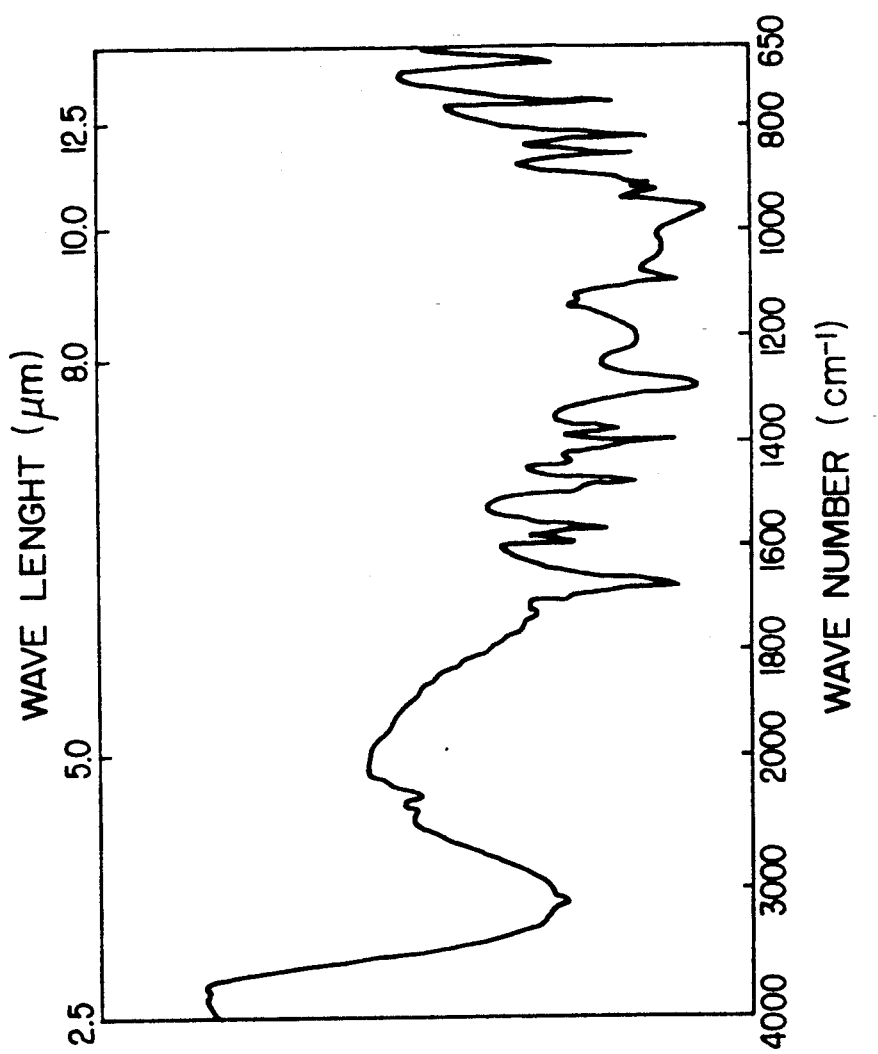
FIG. 2 shows I.R. spectrum of DCAP-P.

U.V. spectrum and IR spectrum are shown in FIGS. 1 and 2, respectively.

EXAMPLE 2

Figure 3:
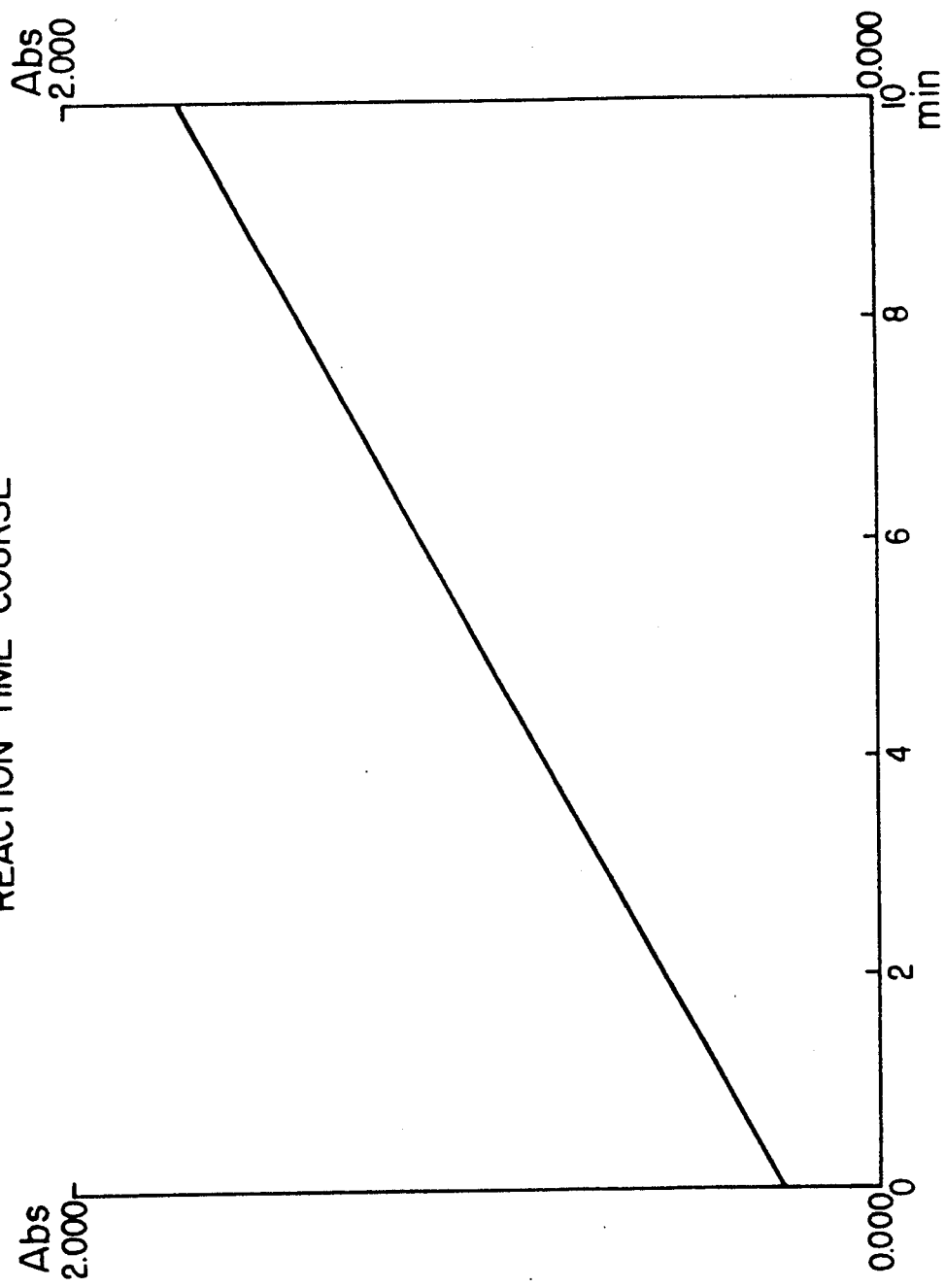
FIG. 3 indicates a reaction time course when DCAP-P is used as substrate.

Method for determination of Acp activity in serum (1) 100 mM citrate buffer solution, pH 5.4 (25° C.)
(2) sample
(3) 7.8 mM substrate (DCAP-P) solution To 2.0 ml of the buffer solution (1) is added 0.1 ml of the sample (2). The mixture is previously warmed at about 37° C. and 0.5 ml of the substrate solution (3) is added thereto. At the same time, a stop watch starts and absorbance at 330 nm is measured accurately one and 2 minutes after. A change in absorbance per minute is thus determined. A time course is shown in FIG. 3.

As the sample, Acp of human prostatic gland origin (manufactured by Sigma Inc.) was used. The Acp activity is calculated by the following equation:

$$IU/l = \frac{\Delta OD/min^{1)} \times \text{total amount of reaction solution} \times 10^6}{\text{molecular extinction coefficient}^{2)} \times \text{amount of sample}}$$

(1) ΔOD/min means a change in absorbance per minute at the measurement wavelength of 330 nm.

(2) Molecular extinction coefficient of 2,6-dichloro-4-acetylphenol at the wavelength of 330 nm is 18500.

According to the above equation, the Acp activity in the sample used was 205 (IU/l). As shown in FIG. 3, linearity was shown for 10 minutes with passage of time. This indicates that automated analysis instruments are usable.

EXAMPLE 3

By changing the pH of the buffer solution (1) in Example 2 from 4.8 to 6.2, the optimum pH of Acp in this method was determined. The conditions were all identical with those of Example 2, except for changing the pH of the buffer solution. The results are shown in FIG. 4. Under the conditions, the optimum pH was 5.4.

EXAMPLE 4

The sample (3), 0.5 ml, of Example 2 was added to 2.0 ml of the buffer solution (1). The mixture was put in a thermostat cell at 37° C. and a change in absorbance at the wavelength of 330 nm was traced with the passage of time to examine stability of the substrate to non-enzymatic hydrolysis. As shown in FIG. 5, the results reveal that the substrate is almost stable up to 10 minutes. Since substrate DCAP-P is stable at the optimum pH of 5.4, it is unnecessary to measure a reagent black for each sample.

EXAMPLE 5

Figure 6:
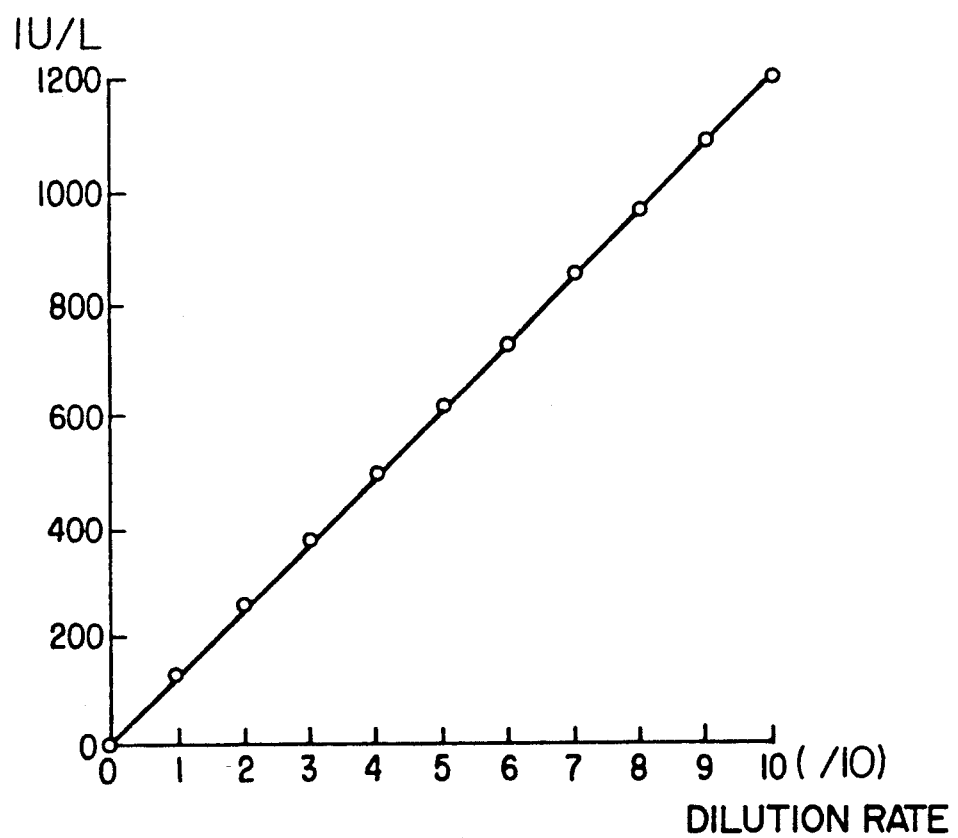
FIG. 6 shows the relationship between Acp dilution rate and enzyme activity.

The relationship between dilution rate of Acp derived from human prostatic gland and enzyme activity was examined (FIG. 6). The dilution of the sample was performed using (1) in Example 2. As shown in FIG. 6, it is revealed that the sample dilution and the enzyme activity are in a linear proportional relationship that passes the origin and the Acp activity can be determined over a wide range of from a low unit to a high unit.

EXAMPLE 6

Figure 7:
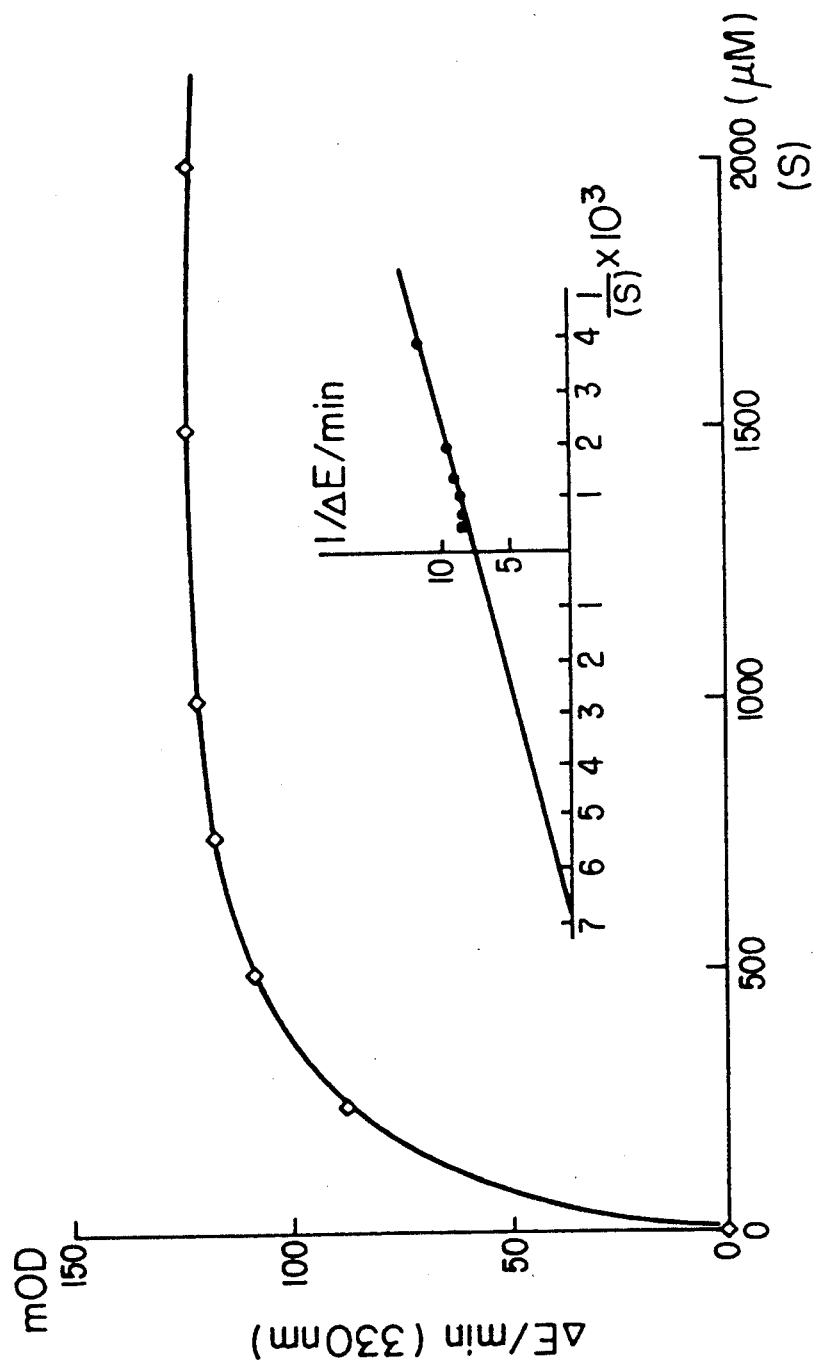
FIG. 7 shows S-V curve and Lineweaver-Burk plots.

Using the sample (3) in Example 2 which was appropriately diluted, a Km value to the substrate was determined from the Lineweaver-Burk plots and found to be 0.14 mM/l (FIG. 7). The results indicate that the affinity of the substrate to Acp is high and is well adoptable to this reaction system.

EXAMPLE 7

Synthesis of 2,6-dibromo-4-acetylphenylphosphoric acid (1) In 5 ml of acetic anhydride was dissolved 5.0 g of 2,6-dibromophenol and, one drop of conc. sulfuric acid was added to the solution. While sometimes manually shaking, the mixture was stirred. When generation of heat stopped, the solution was poured onto 50 ml of ice water and the precipitated crystals of acetic acid-2,6-dibromophenyl were taken by filtration. The crystals were washed with chilled water and dried under reduced pressure. Next, this acetic acid-2,6-dibromophenyl was dissolved in 20 ml of nitrobenzene and 4.0 g of powdery aluminum chloride was gradually added to the solution. The reaction was carried out at 60° to 70° C. for 50 hours to effect Fries rearrangement. After completion of the reaction, the reaction solution was poured onto 100 ml of cold dil. hydrochloric acid. After allowing to stand at 5° C. overnight, the precipitated crystals were taken out by filtration, washed with n-hexane and dried under reduced pressure to give 3.87 g of 2,6-dibromo-4-acetylphenol as crude crystals. The crystals were recrystallized from hot ethyl acetate to give 2.42 g of pure 2,6-dibromo-4-acetylphenol as light brown crystals. 2,6-Dibromo-4-acetylphenol (3,5-dibromo-4-hydroxyacetophenone): $C_8H_6Br_2O_2$ m.p. 180°–183° C.

| | Elemental analysis [%] | |
|---|---|---|
| | Found | Calcd. |
| C: | 32.71 | 32.69 |
| H: | 1.90 | 2.06 |

(2) In acetone was dissolved 2.21 g of 2,6-dibromo-4-acetylphenol and, 3.75 ml of 2N sodium hydroxide aqueous solution was added to the solution under ice cooling. Acetone and ether were again added to the solution The precipitated crystals were taken out by filtration and dried under reduced pressure to give 1.88 g of light yellow 2,6-dibromo-4-acetylphenol sodium salt. Then, 0.90 g of the sodium salt was suspended in 10 ml of n-hexane After cooling the suspension to $-10°$ C., 2 ml of phosphorus oxychloride was dropwise added to the suspension. After the dropwise addition, the temperature of the reaction solution was reverted to room temperature followed by reacting for 20 hours. After the precipitated sodium chloride was removed by filtration, the filtrate was concentrated to give a brown oily substance. To the oily substance was added 50 ml of ice water to perform hydrolysis at 0 to 15° C. for an hour and 30° to 45° C. for an hour. After insoluble matters were removed by filtration, sodium chloride was added to the filtrate to the saturation. Then, the filtrate was extracted with ethyl acetate. After drying over anhydrous magnesium sulfate, ethyl acetate was distilled off to give 323 mg of 2,6-dibromo-4-acetylphenyl-phosphoric acid as crude crystals. The crude crystals were recrystallized from dimethylsulfoxide (DMF) and ether to give 234 mg of pure 2,6- dibromo-4-acetylphenyl-phosphoric acid.½ DMF as light brown crystals $C_8H_7Br_2O_5P.1/2C_3H_7NO$ m.p. 149°–154° C.

|   | Elemental analysis [%] | |
|---|---|---|
|   | Found | Calcd. |
| C: | 28.03 | 27.80 |
| H: | 2.82 | 2.56 |
| N: | 1.75 | 1.71 |

EXAMPLE 8

Synthesis of
2,6-dichloro-4-(n-butyryl)phenylphosphoric acid (1) In 10 ml of n-butyric anhydride was dissolved 10.0 g of 2,6-dichlorophenol and, one drop of conc. sulfuric acid was added to the solution. While sometimes manually shaking a reaction vessel, the mixture was stirred. When generation of heat stopped, the solution was poured onto 100 ml of ice water. The solution was extracted with n-hexane and washed with saturated sodium chloride aqueous solution. After drying over anhydrous magnesium sulfate overnight, n-hexane was distilled off to give 13.22 g of n-butyric acid-2,6-dichlorophenyl as a colorless oily substance. Next, this n-butyric acid-2,6-dibromophenyl was dissolved in 25 ml of nitrobenzene and 13.8 g of powdery aluminum chloride was gradually added to the solution. The mixture was reacted at 55° to 65° C. for 40 hours to effect Fries rearrangement After completion of the reaction, the reaction solution was poured onto 500 ml of cold dil. hydrochloric acid. After allowing to stand at 5° C. overnight, the aqueous phase was separated from the system and the organic phase was extracted with 2N sodium hydroxide aqueous solution. After the extraction, the solution was rendered acidic by adding 5N hydrochloric acid thereto and the precipitated crystals were extracted with ethyl acetate. After washing with saturated sodium chloride aqueous solution, the ethyl acetate phase was dried over anhydrous magnesium sulfate overnight. Then ethyl acetate was distilled off to give 2.09 g of 2,6-dichloro-4-(n-butyryl)phenol as crude crystals. The crystals were recrystallized from ether and n-hexane to give 1.95 g of pure 2,6-dichloro-4-(n-butyryl)phenol as light brown crystals 2,6-Dichloro-4-(n-butyryl)phenol: $C_{10}H_{10}O_2Cl_2$ m.p. 93°–96° C.

|   | Elemental analysis [%] | |
|---|---|---|
|   | Found | Calcd. |
| C: | 51.58 | 51.53 |
| H: | 4.35 | 4.32 |

(2) In acetone was dissolved 2.33 g of 2,6-dichloro-4-(n-butyryl)phenol and, 2 5 ml of 4N sodium hydroxide aqueous solution was added to the solution under ice cooling. Acetone and ether were again added to the solution and the precipitated crystals were taken out by filtration and dried under reduced pressure to give 2.14 g of light brown 2,6-dichloro-4-(n-butyryl)phenol sodium salt. Then, 2.14 g of the sodium salt was suspended in 20 ml of n-hexane After cooling the suspension to $-10°$ C, 7.25 ml of phosphorus oxychloride was dropwise added to the suspension. After the dropwise addition, the temperature of the reaction solution was reverted to room temperature followed by reacting for 24 hours. After the precipitated sodium chloride was removed by filtration, the filtrate was concentrated to give a brown oily substance. To the oily substance was added 75 ml of ice water to perform hydrolysis at 0 to 15° C. for an hour and 40° to 50° C. for an hour. After the reaction, insoluble matters were removed by filtration and sodium chloride was added to the filtrate to the saturation Then, the filtrate was extracted with ethyl acetate. After drying over anhydrous magnesium sulfate, ethyl acetate was distilled off to give 2.06 g of 2,6-dichloro-4-(n-butyryl)phenylphosphoric acid as crude crystals. The crude crystals were recrystallized from DMF and ether to give 1.79 g of pure 2,6-dichloro-4-(n-a butyryl)phenylphosphoric acid. DMF as white crystals. 2,6-Dichloro-4-(n-butyryl)phenylphosphoric acid:

m.p. 78°–80° C.

$C_{10}H_{11}Cl_2O_5P.C_3H_9NO$

|   | Elemental analysis [%] | |
|---|---|---|
|   | Found | Calcd. |
| C: | 40.39 | 40.43 |
| H: | 5.18 | 4.70 |
| N: | 3.61 | 3.63 |

EXAMPLE 9

Figure 8:
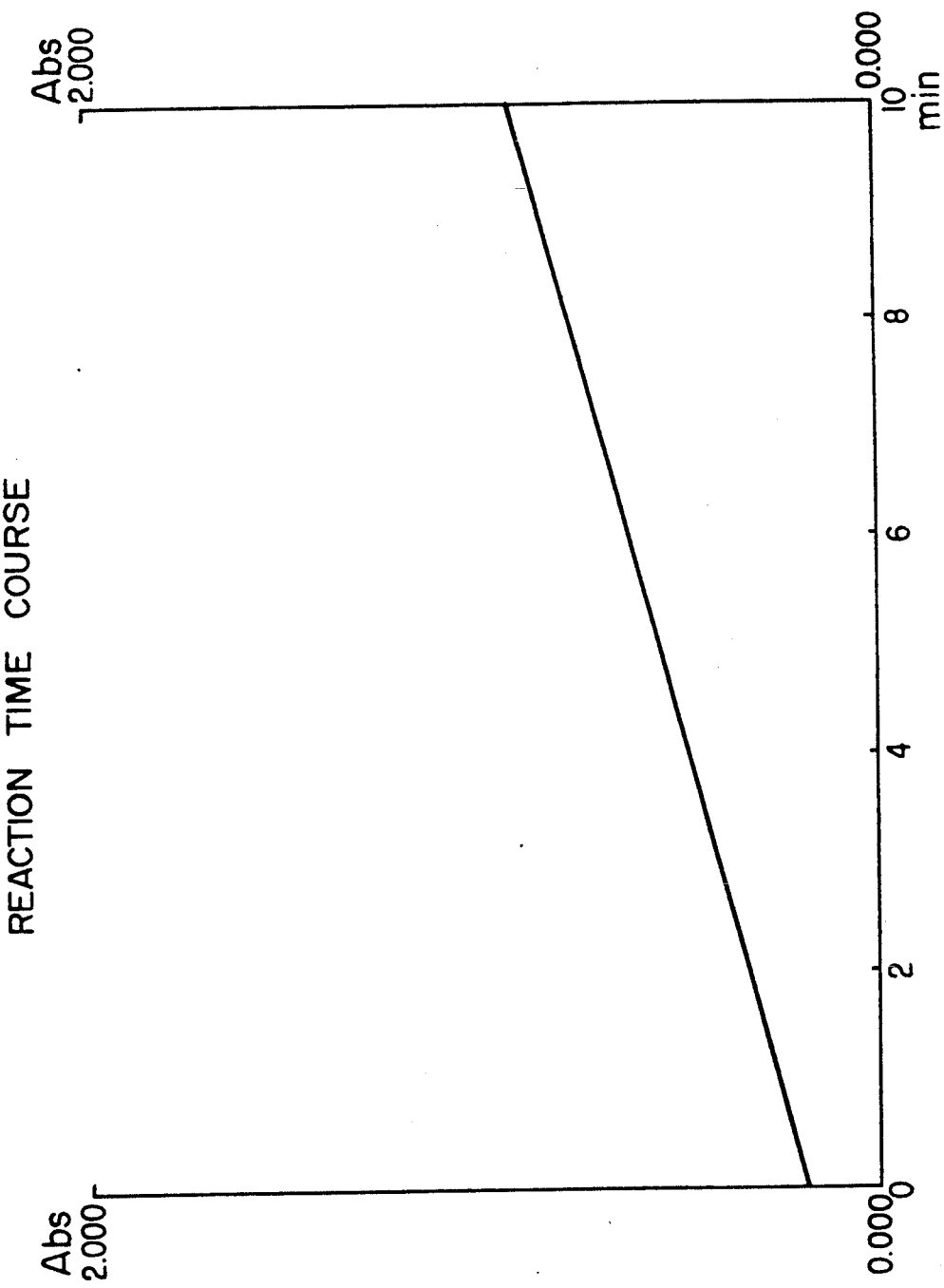
FIG. 8 shows a reaction time course when DBAP-P is used as substrate.
Figure 9:
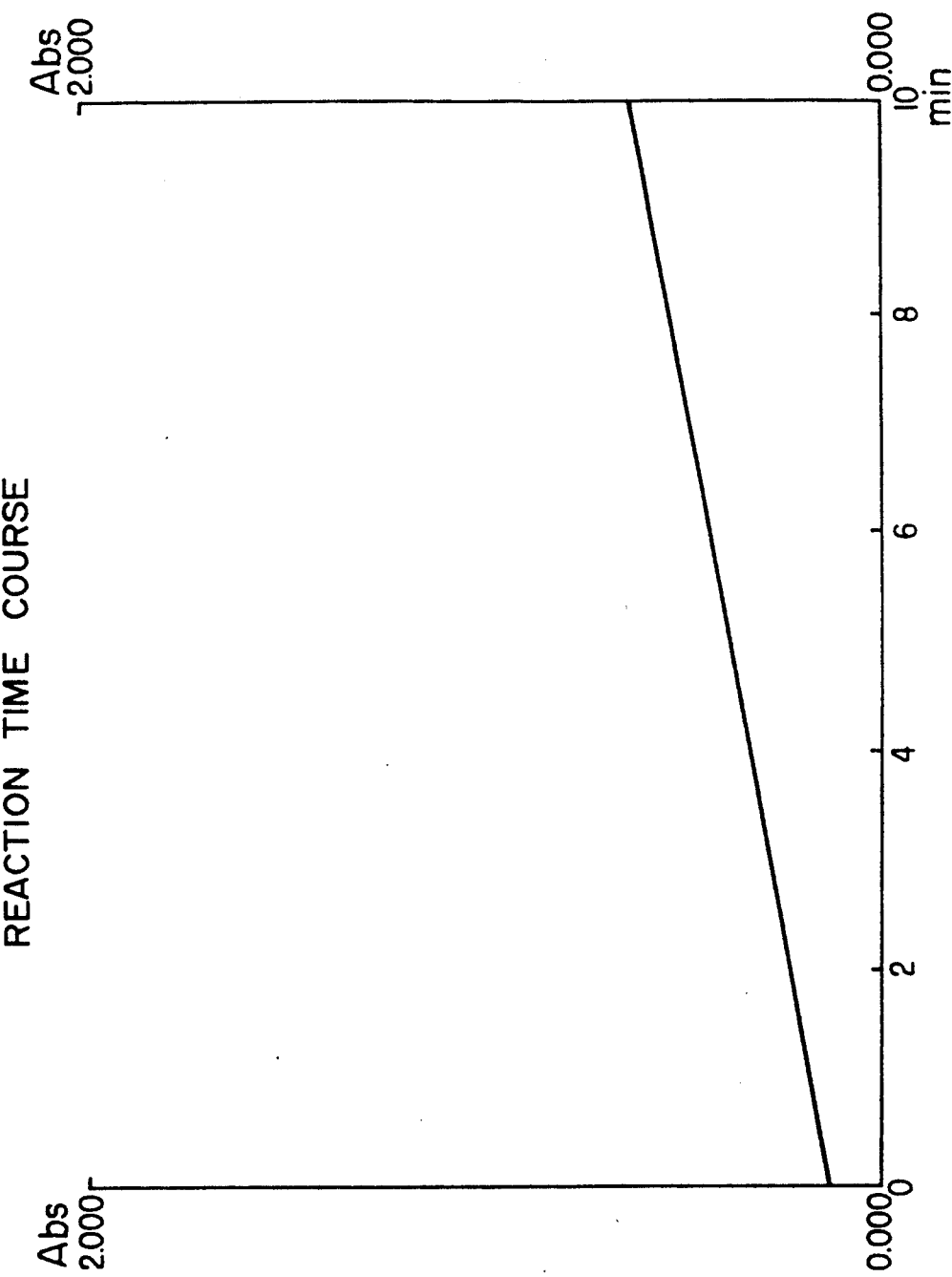
FIG. 9 shows a reaction time course when DCBP-P is used as substrate.

Determination of Acp activity using as substrates 2,2,6-dibromo-4-acetylphenylphosphoric acid and 2,6-dichloro-4-(n-butyryl)phenylphosphoric acid The Acp activity was determined using 2,phoric acid (DBAP-P) and 2,6-dichloro-4-(n-butyryl)phenylphosphoric acid (DCBP-P) in place of the substrate (3) (DCAP-P) in Example 2. Reagents and operation were similar to Example 2. The time courses are shown in FIGS. 8 and 9. The Acp activity of a sample was 103 IU/l with DBAP-P and 109 IU/l with DCBP-P. The molecular extinction coefficients were 18900 and 11200, respectively. As shown in FIGS. 8 and 9, linearity was exhibited for 10 minutes with passage of time. This indicates that these substrates are also applicable to automated analysis instruments.

What is claimed is:

1. A phosphoric acid derivative represented by formula (I):

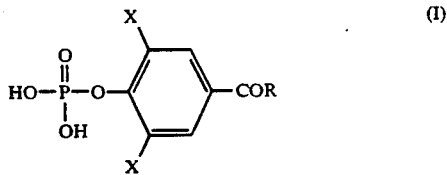

wherein X is a halogen and R is $-(CH_2)_nCH_3$ (n=0 to 3), or salts thereof.

2. A compound of formula (I) as claimed in claim 1, wherein X is chlorine atom or bromine atom.

3. A compound of formula (I) as claimed in claim 1, wherein n is 0 or 3.

4. A compound of formula (I) as claimed in claim 1, which is selected from the group consisting of 2,6-dichloro-4-acetylphenylphosphoric acid, 2,6-dibromo-4-acetylphenylphosphoric acid and 2,6-dichloro-4-(n-butyryl)phenylphosphoric acid.

* * * * *